United States Patent [19]

Takashima et al.

[11] Patent Number: 5,041,079
[45] Date of Patent: Aug. 20, 1991

[54] METHOD FOR REMOVING HUMAN IMMUNODEFICIENCY VIRUS AND/OR ITS RELATED COMPOUNDS

[75] Inventors: Seisuke Takashima; Keiichi Kurokawa; Shuhei Nakaji, all of Kurashiki; Ken Yamane, Hiroshima; Ryosuke Murayama, Kamakura, all of Japan

[73] Assignee: Kuraray Co., Ltd., Kurashiki, Japan

[21] Appl. No.: 277,266

[22] Filed: Nov. 29, 1988

[30] Foreign Application Priority Data

Dec. 4, 1987 [GB] United Kingdom ............... 8728453
Apr. 27, 1988 [JP] Japan ........................... 63-107019

[51] Int. Cl.$^5$ ............................................. A61M 37/00
[52] U.S. Cl. ................................................. 604/5; 604/4; 128/DIG. 3
[58] Field of Search ................. 604/4, 5, 6; 435/235, 435/236, 237, 238, 239

[56] References Cited

U.S. PATENT DOCUMENTS 3,925,152 12/1975 Porath et al. .
3,963,613 6/1976 Chibata et al. .................... 604/5 X
4,215,688 8/1980 Terman et al. ..................... 604/5
4,681,870 7/1987 Balint, Jr. et al. ............ 128/DIG. 3
4,824,432 4/1989 Skurkovich et al. ............... 604/4

FOREIGN PATENT DOCUMENTS 0263934 5/1987 European Pat. Off. .
0135497 10/1979 Japan ................................. 604/5
0226058 10/1986 Japan .
0266072 11/1987 Japan .
2006642A 5/1979 United Kingdom .

OTHER PUBLICATIONS

Abstract of Japanese Laid-Open Patent Publication No. 68527/1988.
Abstract of Japanese Laid-Open Patent Publication No. 93728/1988.
Abstract of Japanese Laid-Open Patent Publication No. 238022/1988.
"The Impact of the AIDS Epidemic on Therapeutic Hemapheresis", Dobri D. Kiprov, M.D., et al., Plasma Therapy, vol. 8, No. 1 (1987), pp. 23-29.
Translation in relevant part of Nikkei New Materials, Jul. 13, 1987.
Abstract of Japanese Laid-Open Patent Publication No. 226058/1986.
Abstract of Japanese Laid-Open Patent Publication No. 266072/1987.
Abstract of "Study of Removal Hepatitis B Antigen Using the Adsorption Method" cited as 6) on p. 9, line 6 of Nikkei New Materials, Jul. 13, 1987 (English translation).

Primary Examiner—Robert A. Hafer
Assistant Examiner—Kerry Owens
Attorney, Agent, or Firm—Burns, Doane, Swecker & Mathis

[57] ABSTRACT

The present invention provides removing agents comprising a solid substance with a weakly acidic or weakly alkaline surface. Since the removing agents can be used for treating body fluid of a patient by, for example, extra-corporeal circulation system thereby effectively removing human immunodeficiency virus and/or its related compounds contained in the body fluid, it is expected that the life of the patient could be prolonged. The significance of the present invention therefore is great.

5 Claims, 1 Drawing Sheet

METHOD FOR REMOVING HUMAN IMMUNODEFICIENCY VIRUS AND/OR ITS RELATED COMPOUNDS

BACKGROUND OF THE INVENTION

1. Field of the Invention

This invention relates to a method for removing human immunodeficiency virus (hereinafter abbreviated as HIV) and/or its related compounds from body fluids of patients.

2. Description of the Prior Art

HIV has affinity for human lymphocytes, particularly for helper T lymphocytes, and tends to invade these lymphocytes and destroy them, thus lowering the function of cell-mediated immunity. As a result, the patients often suffer from opportunistic infection or benign or malignant tumor, which is usually fatal.

Research is actively under way to find effective remedies for infection caused by HIV. For example, attempts have been made to prepare an effective vaccine, but construction of a vaccine is difficult in obtaining the correct antigen (the target of the vaccine) because the HIV gene is likely to undergo mutation. Administration of Suramin, HPA 23 and AZT was also attempted based on the concept that a specific inhibitor against reverse transcriptase and/or DNA synthesis inhibitor of HIV could retard the settlement of the viral genome. However, no satisfactory results have been obtained, with only side effects of these compounds being reported. It is conceivable that antiviral agents like interferons could retard the assembly of retroviruses and they are presently in use as immune-controlling agents; actually, however, no marked effect has been observed in clinical tests.

An increase in the amount of immune complexes and the presence of inhibitory factors derived from interleukin-2 were observed in the plasma of HIV-infected patients, and plasmapheresis has been tried to remove these substances. But no satisfactory result have yet been obtained [Plasma Therapy, 8, 23 (1987)]. Many different kinds of therapy have been attempted to cure infections caused by HIV, as described above, but only limited effects, if any, were exhibited by any of these therapies.

SUMMARY OF THE INVENTION

Based on the information that HIV is released in large quantities from T cells into body fluids of HIV-infected patients, particularly those in the aggravating period, the inventors considered that, if the amount of HIV and/or its related compounds in their body fluid (e.g. blood, serum, plasma, cerebrospinal fluid, etc.) can be reduced by the extracorporeal blood circulation system, this might prevent their clinical condition from worsening, thus prolonging their lives.

Accordingly, an object of this invention is to provide a method for removing HIV and/or its related compounds from the body fluid.

This object can be achieved by a method which comprises employing a solid substance with a weakly acidic or weakly alkaline surface to remove HIV and/or its related compounds from body fluids.

BRIEF DESCRIPTION OF THE DRAWINGS

A more complete appreciation of the invention and many of the advantages thereof will be readily ascertained as the same become better understood by reference to the following detailed description when considered with the accompanying drawings, wherein.

DETAILED DESCRIPTION OF THE INVENTION

Figure 1:
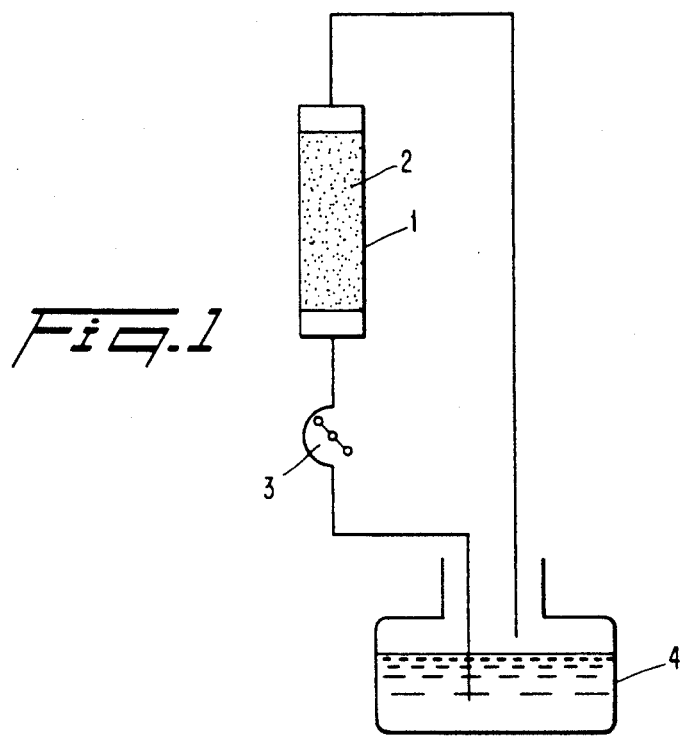
FIG. 1 shows diagrammatically an example of circulation systems which purify HIV-containing body fluids using a solid substance with a weakly acidic or weakly alkaline surface.

The present invention is characterized by employment of a solid substance with a weakly acidic or weakly alkaline surface for the purpose of removing HIV and/or its related compounds in the body fluid of HIV-infected patients.

The solid substances with a weakly acidic or weakly alkaline surface used in this invention are those that show a weakly acidic or weakly alkaline reaction when a pH reagent is dropped onto their surface. Weak acidity herein means a pH level in the range 2.5 to 6.9, and weak alkalinty a pH level in the range 7.4 to 10.5. Substances whose surface pH is in the range 7.0 to 7.3 (e.g. nonpolar polypropylene, quartz and cation-exchange resins of $SO_3Na$-type) are unable to absorb HIV and/or its related compounds, while substances whose surface pH is less than 2.5 (e.g. strongly acidic cation-exchange resins) or higher than 10.5 (e.g. strongly basic anion-exchange resins) tend to coagulate proteins contained in body fluids and hence fail to remove HIV and/or its related compounds efficiently.

As examples of the solid substances with a weakly acidic or weakly alkaline surface used in this invention, there may be mentioned inorganic substances, such as calcium phosphate (e,g, hydroxyapatite), alumina, silica, silica-alumina and zirconia; and polymers bearing polar groups, such as anion-exchange resins ($NH_2$-type), cation-exchange resins (COOH- and $SO_3H$-types), sulphonated, carboxyl-containing or amino-containing polyolefins, sulphonated polystyrene, and insoluble sulphonated, carboxyl-containing or amino-containing polyvinyl alcohols crosslinked with an aldehyde. Each of these substances may be used alone in any desired form (e.g. as granules), or may be supported on an less active or inactive carrier (e.g. porous glass). Further, polyhydroxyethylmethacrylate, polyacrylic acid, heparin or dextran sulphate supported on the carrier may be used. As mentioned above, in the present invention various solid substances with a weakly acidic or weakly alkaline surface are used. Solid substances with a weakly acidic surface are preferred, e.g. cation-exchange resins ($SO_3H$-and COOH-types), silica-alumina and 3-component calcined product of hydroxyapatite-silica-alumina, among which silica-alumina and 3-component calcined product of hydroxyapatite-silica-alumina are more preferred because of their large surface area, the latter being still more preferred since it is excellent in biocompatibility.

Any solid substances in which weak acidity or alkalinity is exhibited only at the surface may be used for the purpose of this invention, except those that are soluble in body fluid. These solid substances may either be porous or nonporous.

Since adsorption of HIV and/or its related compounds takes place on the surface of the solid substance, the internal structure of the solid may be any type and may be made of different material from the surface. The agents for removing HIV and/or its related compounds of this invention may be of any desired shape, such as powder, granules, plates and fibers, but are usually in the form of granules with a diameter in the range 0.1 to 5 mm. In addition, these granules should preferably be spherical to mimimize possible damages to hematocytes, because the agent is brought into direct contact with hematocytes in some cases.

It has been unexpectedly found that treating body fluids (e.g. blood, surum, plasma, cerebrospinal fluid, etc.) of a patient with an agent comprising a solid substance as defined above efficiently removes HIV and/or its related compounds contained therein through adsorption. "HIV-related compounds" herein means metabolites produced by cells attacked by HIV, and immunosuppresive factors, i.e. substances that retard the activity of immunocompetent cells produced upon invasion of viruses.

The agent comprising a solid substance used in accordance with this invention is charged to a column for service. The column used for this purpose should preferably be provided with an inlet and an outlet designed to allow easy connection with the blood circuit, and with a filter made of, for example, polyester and set between the inlet and the agent layer, and between the outlet and the agent layer. The column may be made of glass, polyethylene, polypropylene, polycarbonate, polystyrene or polymethyl methacrylate. Of these, polypropylene and polycarbonate are preferred materials, because the column packed with the agent is sterilized (e.g. autoclave and γ-ray sterilization) before use.

FIG. 1 shows diagrammatically an example of circulation systems which purify HIV-containing body fluid using a solid substance with a weakly acidic or weakly alkaline surface. In FIG. 1, numeral 1 is a column packed with the solid substace 2, numeral 3 is a pump for circulating fluid and 4 is HIV cultured fluid.

HIV and/or its related compounds can be removed from body fluids of patients by the extracorporeal blood circulation system using a packed column as described above. The following two types of extracorporeal blood circulation system are mentioned.

(1) Blood taken from a blood vessel of a patient is forced to pass through a column packed with the agent of this invention to remove from the blood, HIV and/or its related compounds, and the clarified blood from the column is returned to the blood vessel of the patient.

(2) Blood taken from a patient is first separated through a separation membrane, by centrifugation or the like into hemocytes and plasma, the plasma thus separated is then forced to pass through a column packed with the agent of this invention to remove from the plasma, HIV and/or its related compounds, the clarified plasma from the column is mixed with the hemocytes separated above, and the mixture is returned to the blood vessel of the patient.

Figure 2:
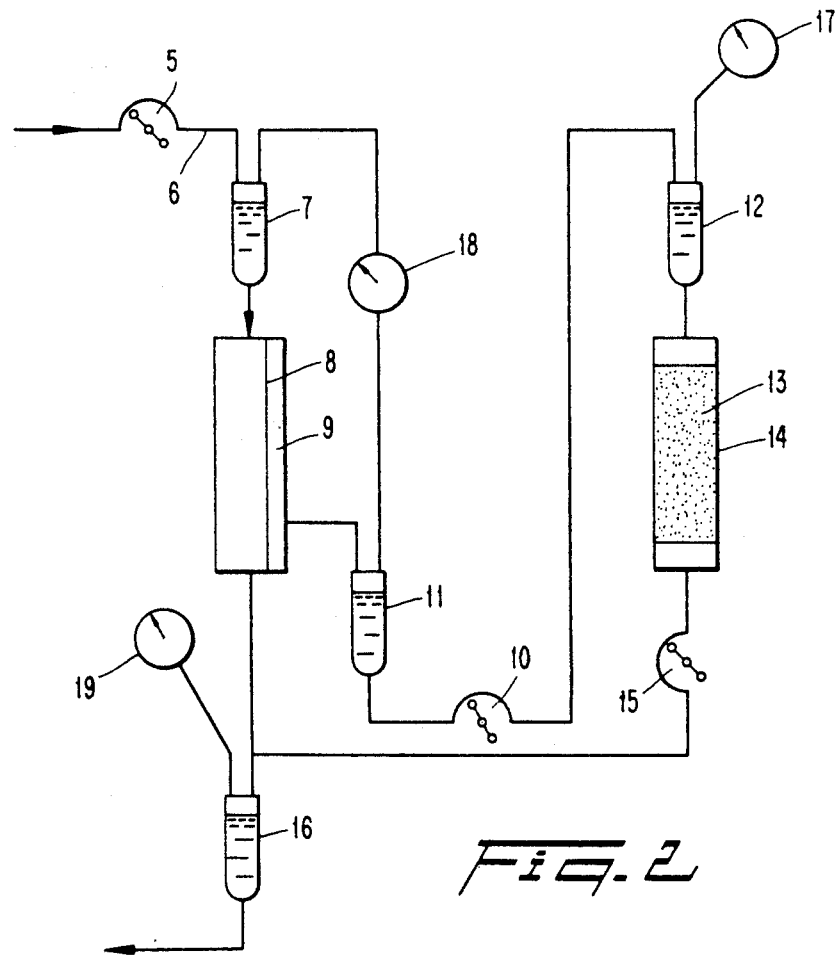
FIG. 2 shows diagrammatically an example of circulation systems which first separate HIV-containing blood into hemocytes and plasma by using a separation membrane, purify the plasma by using a solid substance with a weakly acidic or weakly alkaline surface and thereafter mix the purified plasma with the hemocytes separated above, followed by returning the mixture to the patient.

Systen (1) may utilize the circulation system shown in FIG. 1. System (2) is shown in FIG. 2. The blood of a patient is introduced using a pump 5 from blood introducing circuit 6 via a blood reservoir 7 into a hemocytes-plasma separator 9 containing therein a separation membrane 8, where the hemocytes and plasma are separated from each other. The plasma is sent through pump 10 via blood reservoirs 11 and 12 to a column 14 packed with the removing agent 13. HIV is removed in the column. The plasma thus clarified is mixed with the hemocytes again and the mixture is returned to the patient via blood reservoir 16 by using pump 15. Numerals 17, 18 and 19 indicate pressure gauges. While the plasma is fed from the top of column 14 in FIG. 2, it may be fed from the bottom.

Of the two methods described above, the latter is more practical because of the samller loss of hemocytes for example, by adhesion of platelets and hemocytes of erythrocytes).

Such treatments as described above remove HIV and/or its related compounds from body fluids or patients, thereby preventing their clinical conditions from worsening and prolonging their lives. In the aggravating period, HIV is released in large quantities from T cells as stated above, and hence this adverse tendency can be repressed if HIV is efficiently removed. Removal of the related compounds will also suppress the antigen-antibody reactions caused by these compounds and allow freedom from suppressing growth of lymphocytes, thus preventing the patient's clinical condition from worsening. It should be noted here that such treatments can also remove useful components in body fluids. If this happens, it is preferable that supplements of these useful components be given to the patients.

Other features of the invention will become apparent in the course of the following descriptions of exemplary embodiments which are given for illustration of the invention and are not intended to be limiting thereof.

EXAMPLES

Examples 1 to 8 and Comparative Examples 1 to 3

(1) Specifications of agents for removing HIV and/or its related compounds:

Test exerpiments were conducted using agents therefor the specifications shown Table 1.

(note) Measurement of surface pH: Each agent was placed on a glass plate, a pH reagent was dropped on it, and surface pH was measured by colorimetry using a pH meter of Kyowa Rikagaku Kenkyusho.

TABLE 1

| No. | Agent | Specification | Surface pH |
|---|---|---|---|
| Comp. Ex. 1 | Polypropylene | Nonpolar powder (av. size: 0.75 mm) | 7.0 |
| Comp. Ex. 2 | Quartz | Quartz powder with its surface treated with a silane coupling agent (av. size: 0.005 mm) | 7.0 |
| Comp. Ex. 3 | Cation-exchange resin | SO$_3$Na-type; IR120B of Japan Organo Co.; Granules (size: 0.6 mm, surface area ≦ 0.1 m$^2$/g) | 7.0 |
| Example 1 | Hydroxyapatite | Granules (size: 0.45 mm, surface area: 100 m$^2$/g); Ca/P: 1.64, calcination temp.: 550° C. | 6.5 |
| Example 2 | Hydroxyapatite | Granules (size: 0.45 mm, surface area: 80 m$^2$/g); Ca/P: 1.64, calcination temp.: 700° C. | 8.5 |
| Example | Silica-alumina | Product of Davison Chemical Co.; granules (size: | 3.0 |

TABLE 1-continued

| No. | Agent | Specification | Surface pH |
|---|---|---|---|
| 3 | | 0.45 mm, surface area: 140 m²/g); Si/Al: 4.4 | |
| Example 4 | Anion-exchange resin | NH₂-type; IRA401 of Japan Organo Co.; Granules (size: 0.6 mm, surface area ≦ 0.1 m²/g) | 8.5 |
| Example 5 | Cation-exchange resin | COOH-type; IRC84 of Japan Organo Co.; Granules (size: 0.6 mm, surface area ≦ 0.1 m²/g) | 3.0 |
| Example 6 | Cation-exchange resin | SO₃H-type; IR120B of Japan Organo Co.; Granules (size: 0.6 mm, surface area ≦ 0.1 m²/g) | 3.0 |
| Example 7 | Alumina | Granules (size: 0.45 mm, surface area: 100 m²/g); calcination temp.: 900° C. | 5.0 |
| Example 8 | Alumina | Granules (size: 0.45 mm, surface area: 100 m²/g); calcination temp.: 1200° C. | 10.0 |

(2) Procedure for removing HIV and/or its related compounds:

Culture supernatant of HIV-infected cells [HIV cell line H9 (possessed by NCI of the United States) was inoculated into sensitive cells CEM (CCRF, CEM, Flow Laboratories, ATCC No. 19, Acute Lymphoblastic Leukemia), followed by multiplication and subculture] was treated with each of the agents mentioned above according to the procedure detailed below.

(i) The agent (0.5 g) was immersed in 2 ml of RPMI-1640 medium, and the mixture was deaerated by heating and subjected to steam sterilization at 121° C. for 20 minutes in a tightly stoppered container.

(ii) Culture supernatant of HIV-infected cells obtained after centrifugal separation at 2000 rpm for 15 minutes was filtered through a 0.45 μm filter, and the filtrate (4 4 ml) was mixed with 16 ml RPMI-1640 medium.

(iii) Supernatant (2 ml) of the mixture obtained in (ii) was added to the mixture obtained in (i), and the resulting mixture was allowed to stand at room temperature for 30 minutes.

(iv) Supernatant of the mixture obtained in (iii) was filtered through a 0.45 μm filter.

(v) A portion (10 μl) of 0.5 ml of the filtrate obtained in (iv) was added to a culture liquid [obtained by incubation of cord blood lymphocytes ($5 \times 10^5$ cells per ml) at 37° C. for 48 hours in the presence of interleukin-2 and phytohemagglutinin (PHA), followed by incubation on a 96-well mulit-titre plate in a total amount of 100 μl], and the mixture was incubated at 37° C, for a predetermined time (3 to 5 days). Three such plates were prepared.

(vi) The sample obtained in (v) was centrifuged for 10 minutes at 1000 G, and the supernatant was filtered through a 0.45 μm filter.

(vii) The filtrate obtained above was used for antigen measurement, and the residue was spread on a slide glass and subjected to testing by the indirect immunofluorescence technique.

(viii) As control samples (for sensitivity measurement) against the above specimen obtained through procedure (ii) to (vii), a specimen obtained by inoculating the culture supernatant of HIV-infected cells onto CEM cells was immersed in RPMI-1640 medium at concentrations of $10^{-1}$, $10^{-2}$, $10^{-3}$, $10^{-4}$ and $10^{-5}$, and the samples thus prepared were submitted to testing by the indirect immunoflorescence technique.

(3) Verification of the effect to remove HIV and/or its related compounds:

(A) Measurement of antigen concentration. The concentration of antigen in culture liquid was determined by ELISA according to the procedure given below using HIV antigen measuring kit (du Pont):

(i) Test sample (180 μl) was mixed with 5% aqueous solution of Triton X-100 (20 μl) on a microplate.

(ii) The mixture was allowed to stand overnight at room temperature.

(iii) Automatic washing with water was repeated three times.

(iv) A solution of biotin-treated antibody (100 μl) was added, and the mixture was incubated at 37° C. for two hours.

(v) Automatic washing.

(vi) HRP (horse-radish peroxidase)-streptoavidin (100 μl) was added, and the mixture was incubated for 15 minutes.

(vii) After automatic washing, 100 μl of an aqueous solution of OPD (o-phenylenediamine) substrate was added.

(viii) 4N-H₂SO₄ solution (50 μl) was added to terminate the reaction.

(ix) Absorbence at 492 nm (620 nm for blank) was measured, and HIV concentration in ng/ml was calculated from a calibration curve.

The results obtained are summarized in Table 2.

TABLE 2

| No. | Agent (surface pH) | Antigen Concn. (ng/ml) After 3 days | After 5 days |
|---|---|---|---|
| — | Positive control | 0.520 | 0.942 |
| — | Negative control | 0 | 0 |
| Comp. Example 1 | Polypropylene (7.0) | 0.490 | 0.936 |
| Comp. Example 2 | Quartz (7.0) | 0.500 | 0.910 |
| Comp. Example 3 | IR-120B (SO₃Na-type) (7.0) | 0.430 | 0.800 |
| Example 1 | Hydroxyapatite (6.5) | 0.351 | 0.570 |
| Example 2 | Hydroxyapatite (8.5) | 0.189 | 0.294 |
| Example 3 | Silica-alumina (3.0) | 0.074 | 0.122 |
| Example 4 | Anion-exchange resin [NH₂-type] (8.5) | 0.373 | 0.608 |
| Example 5 | Cation-exchange resin [COOH-type] (3.0) | 0.114 | 0.164 |
| Example 6 | Cation-exchange resin [SO₃H-type] (3.0) | 0 | 0 |
| Example 7 | Alumina (5.0) | 0.341 | 0.492 |
| Example 8 | Alumina (10.0) | 0.180 | 0.272 |

As is seen from Table 2, little or no HIV antigen (p 24) was adsorbed with polypropylene, quartz and a cationexchange resin of SO₃Na-type, all of which have a neutral surface. On the other hand, it was observed that removing agents having a weekly acidic or weakly alkaline surface had removed antigen by adsorption. In particular, cation-exchange resins of SO₃H-type and COOH-type and removing agents such as silica-alumina, having a weakly alkaline surface showed marked ability to remove antigen, i.e. to remove HIV.

(B) Evaluation by the indirect immunofluorescence technique. Presence or absence of HIV and/or its related compounds in the residue separated in (2) above (Procedure for removing HIV and/or its related compounds) was determined by the indirect immunofluorescence technique as described below, and the effectiveness of the agents was evaluated based on the result obtained.

(i) Each of the residues obtained in the HIV adsorbing operation ((2)(i)–(vii)) was washed with 1 ml PBS for one minute at a low revolution speed.

(ii) The washed residue was suspended in 50μl PBS, and two spots of the suspension thus obtained were placed on a slide glass for measuring HIV antigen.

(iii) The spots on the slide glass were fixed by immersion in methanol.

(iv) The fixed spots were dehydrated by addition of acetone, followed by air drying.

(v) The patient serum containing HIV antibody or mouse monoclonal HIV (p24) antibody - PBS solution (volume ratio; 1:40) (20μl) was added to each spot.

(vi) The spots thus treated were incubated at 37°C. for 20 minutes and then washed with PBS solution for 20 minutes.

(vii) Human anti-IgG antibody or mouse anti-IgG antibody-PBS solution (volume ratio; 1:20) (20μl) was added to each spot.

(viii) The spots thus treated were incubated at 37°C. for 20 minutes and then washed with PBS solution for 20 minutes.

(ix) Streptoavidin-fluorescein - PBS solution (volume ratio; 1:50) (20μl) was added to each spot.

The spots thus treated were incubated at 37°C. for 10 minutes and then washed with PBS solution in a dark box.

(xi) One drop of a mixture of 90% glycerol and 10% PBS solution was added to each spot.

(xii) Presence or absence of fluorescence at each spot was observed with a microscope under ultroviolet irradiation.

The result is shown in Table 3.

8. Though it was not negative in Examples 1 and 4, the production of antigen in these examples was less than that in comparative examples. After five days' incubation, production of antigen was not positive on Examples 3, 5 and 6. On the other hand, production of antigen was observed on Examples 1, 2, 4, 7 and 8. This indicates that an extremely small amount of HIV left unadsorbed produced a detectable quantity of antigen after five days' incubation, showing the slightly lower ability of these substances (Examples 1, 2, 4, 7 and 8) to remove HIV and/or its related compounds than the others.

(c) Evaluation of the ability to remove HIV and/or related compounds based on the intake of a thymidine derivative into lymphocytes of cord blood. The culture liquid, sensitized by CEM cells and treated with each of the above-mentioned agents for removing HIV and/or related compounds was tested for the intake of a thymidine derivative by lymphocytes to evaluate the effects of the removing agents according to the procedure given below.

(i) Lymphocytes taken from the cord blood of a newborn was diluted to a concentration of $5 \times 10^5$ cell/ml.

(ii) This suspension of lymphocytes was added to RPMI-1640 medium containing 10% fetal bovine serum (FBS), 100 IU/ml penicillin, 100μg/ml streptomycin, 1% PHA and 1 unit/ml interleukin-2 (IL-2), and the mixture was incubated at 37°C. for 48 hours.

(iii) The culture liquid thus obtained (80 μl) in (ii) was mixed with each of the samples sensitized with CEM cells and treated above with the agent for removing HIV and/or its related compounds (20 μl), and the mixture was incubated for three or five days.

(iv) To the mixture incubated in (iii) above, was, added a radioactive thymidine derivative [monoammonium (methyl-1', 2'-$^3$H)-thymidime-5'-triphosphate, $^3$H-dTTP] (1 μCuri/well) six hours before the end of incubation.

(v) After incubation, the thus treated lymphocytes were collected on a Wattman glass filter ® by filtration,

TABLE 3

| No. | Agent (surface pH) | Indirect immuno fluorescence | |
|---|---|---|---|
| | | After 3 days | After 5 days |
| — | Positive control | + | + |
| — | Negative control | — | — |
| Comp. Ex. 1 | Polypropylene (7.0) | + | + |
| Comp. Ex. 2 | Quartz (7.0) | + | + |
| Comp. Ex. 3 | IR-120B (SO$_3$Na-type) (7.0) | ± | + |
| Example 1 | Hydroxyapatite (6.5) | ± | + |
| Example 2 | Hydroxyapatite (8.5) | — | + |
| Example 3 | Silica-alumina (3.0) | — | — |
| Example 4 | Anion-exchange resin (NH$_2$-type) (8.5) | ± | + |
| Example 5 | Cation-exchange resin (COOH-type) (3.0) | — | ± |
| Example 6 | Cation-exchange resin (SO$_3$Na-type) (3.0) | — | — |
| Example 7 | Alumina (5.0) | — | + |
| Example 8 | Alumina (10.0) | — | + |

Diluted samples*:

| $C(+) \times 10^{-1}$:+ | $C(+) \times 10^{-2}$:+ | $C(+) \times 10^{-3}$:+ | $C(+) \times 10^{-4}$:+ | $C(+) \times 10^{-5}$:+ |

*Samples obtained by diluting positive control [C(+)] with RPMI medium to $10^{-1}$, $10^{-2}$, $10^{-3}$, $10^{-4}$ and $10^{-5}$ concentrations (after three days' incubation).

Antigen was detected in samples prepared by diluting positive control [C(=)] down to $10^{-5}$ concentration, indicating the high sensitivity of this method. As can be seen from Table 3, antigen production was negative (—) after three days' incubation in Examples 2, 3, 5, 6, 7 and washed with 5% aqueous solution of trichloroacetic acid (10 ml) and then with methanol (10 ml), and air-dried.

(vi) The glass filter with lymphocytes collected thereon was put in a polyethylene container, an extraction agent (main component: toluene) was added, and the amount of $^3$H-dTTP taken in by the lymphocytes was measured by using a scintillation counter.

The ability of agents to remove HIV and/or its related compounds was evaluated based on the intake of $^3$H-dTTP using the amount taken in by negative control [C(−)] as standard.

The results are shown in Table 4.

TABLE 4

| No. | Agent (surface pH) | Intake of $^3$H-dTTP (%) After 3 days | After 5 days |
|---|---|---|---|
| — | Positive control | 50.6 | 20.9 |
| — | Negative control | 100 | 100 |
| Comp. Example 1 | Polypropylene (7.0) | 45.3 | 22.7 |
| Comp. Example 2 | Quartz (7.0) | 46.0 | 22.0 |
| Comp. Example 3 | IR-120B (SO$_3$Na-type) (7.0) | 43.0 | 25.0 |
| Example 1 | Hydroxyapatite (6.5) | 92.9 | 82.0 |
| Example 2 | Hydroxyapatite (8.5) | 109.3 | 77.6 |
| Example 3 | Silica-alumina (3.0) | 96.1 | 78.4 |
| Example 4 | Anion-exchange resin [NH$_2$-type] (8.0) | 100.3 | 68.7 |
| Example 5 | Cation-exchange resin [COOH-type] (3.0) | 103.2 | 91.9 |
| Example 6 | Cation-exchange resin [SO$_3$H-type] (3.0) | 78.8 | 75.5 |
| Example 7 | Alumina (5.0) | 98.5 | 67.1 |
| Example 8 | Alumina (10.0) | 98.5 | 72.3 |

As is apparent from Table 4, the intake of the thymidine derivative by positive control [C(=)] was reduced to about half that with negative control [C(−)] after three days of incubation. this indicates that lymphocytes are destroyed by HIV, leading to reduction in intake of thymidine derivative. This tendency is more marked after five days' incubation. When HIV culture liquid is treated with the agents for removing HIV and/or its related compounds no significant reduction in the intake of thymidine derivative is observed after three and five days' incubation, compared with positive control and neutral removing agents. This suggests that agents with a weakly acidic or alkaline surface have removed not only HIV but also those substances which participate in the destruction of lymphocytes by HIV.

The result shown in Table 4 is nearly in agreement with the results of Tables 2 and 3. There are some agents, however, which are not so significant their ability of removing HIV (Table 2) but show high survival rate of lymphocytes in Table 4 (for example, Example 1). This also suggests the ability of agents to remove not only HIV but the related compounds through adsorption.

(D) Evaluation of the ability to remove HIV and/or its related compounds by a batch method. Concentrations and productions of HIV antigen after 7 days and 14 days were measured using CEM cell in the same manner as in (A) and (B) according to the procedure shown below.

(i) Supernatant of HIV culture liquid (2 ml) was added to 2 ml of each of the removing agents (0.5 g) /RPMI-1640 and the mixture was stirred for 30 minutes.

(ii) Supernatant of (i) was taken and filtered through a 0.45 μm membrane filter.

(iii) From the filtrate obtained above, 0.5 ml was taken as a specimen for determining antigen.

(iv) The filtrate (0.2 ml) of (iii) was inoculated on a culture liquid (1.8 ml) of CEM cell (5×10$^5$ cell/ml)-RPMI-1640 and the mixture was incubated in a carbon dioxide gas incubator.

(v) Four days after inoculation, the culture supernatant (1 ml) was taken and fresh RPMI-1640 culture liquid (1 ml) was added thereto.

(vi) Then, seven days after inoculation, the culture liquid (1 ml) was taken and fresh RPMI-1640 culture liquid (1 ml) was added thereto. The culture supernatant was subjected to determination for antigen concentration and for antigen production by HIV on CEM cells according to indirect immuno-fluorescence technique.

(vii) The same procedure as (v) was repeated 11 days after inoculation.

(viii) The same procedure as (vi) was repeated 14 days after inoculation to determine antigen concentration and antigen production.

The results are shown in Table 5.

TABLE 5

| No. | Agent | Days after incubation | Evaluated by | Dilution ratio 10$^0$ | 10$^{-1}$ | 10$^{-2}$ | 10$^{-3}$ | 10$^{-4}$ | 10$^{-5}$ |
|---|---|---|---|---|---|---|---|---|---|
| Comp. Ex. 1 | Polypropylene | 7 | (a) | + | / | / | / | / | / |
| | | | (b) | ≥1.2 | / | / | / | / | / |
| | | 14 | (a) | + | + | + | + | + | + |
| | | | (b) | ≥1.2 | ≥1.2 | ≤0.03 | ≤0.03 | ≤0.03 | ≤0.03 |
| Example 3 | Silica-alumina | 7 | (a) | + | / | / | / | / | / |
| | | | (b) | 0.31 | / | / | / | / | / |
| | | 14 | (a) | + | + | ± | − | − | − |
| | | | (b) | 0.28 | 0.04 | ≤0.03 | ≤0.03 | ≤0.03 | ≤0.03 |
| Example 5 | Cation-exchange resin (COOH-type) | 7 | (a) | + | / | / | / | / | / |
| | | | (b) | 0.50 | / | / | / | / | / |
| | | 14 | (a) | + | + | ± | − | − | − |
| | | | (b) | 0.25 | ≤0.03 | ≤0.03 | ≤0.03 | ≤0.03 | ≤0.03 |
| Example 6 | Cation-exchange resin (SO$_3$H-type) | 7 | (a) | − | / | / | / | / | / |
| | | | (b) | ≤0.03 | / | / | / | / | / |
| | | 14 | (a) | − | − | − | − | − | − |
| | | | (b) | ≤0.03 | ≤0.03 | ≤0.03 | ≤0.03 | ≤0.03 | ≤0.03 |

Note:
Evaluation method
(a): indirect immunofluorescence technique
(b): antigen concentration measurement
Antigen concentrations are in ng/ml.

Using HIV - RPMI-1640 culture liquid, sensitivity of HIV antigen concentration was tested by using an indirect immunofluorescence technique and with a du Pont kit. The results are shown in Table 6.

TABLE 6

| Dilution ratio | Antigen concentration* | Indirect immunofluorescence techinque |
|---|---|---|
| $10^0$ | $\geq 1.2$ | + |
| $10^{-1}$ | 0.16 | + |
| $10^{-2}$ | $\leq 0.03$ | + |
| $10^{-3}$ | " | + |
| $10^{-4}$ | " | + |
| $10^{-5}$ | " | + |
| $10^{-6}$ | " | ± |

*in ng/ml

The threshold of measurement for antigen concentration is 0.03 ng/ml, and hence the concentration measurement does not work at dilution ratios of $10^{-2}$ to $10^{-3}$, while the threshold by the indirect immunofluorescence technique is $10^{-5}$. Evaluation of one and the same specimen by two different methods therefore is very important. The measurement of antigen concentration by using the kit is to determine HIV (p24), and by this technique HIV (p24) can be detected as long as it is present in culture supernatant whether or not it has activity. Thus, the ability for HIV antigen production of the specimen solutions which had been treated with silica-alumina and ion-exchange resins (COOH type and SO₃H type) studied above decreased to about $10^{-2}$ to $10^{-3}$ compared to the original HIV - RPMI-1640 solution, showing their excellent HIV removing abilities.

(E) Evaluation of the ability to remove HIV antigen and/or its related compounds. The HIV culture liquid containing fetal bovine serum (FBS) was circulated through a column (minimodule) filled with the above-mentioned agents, as stated below, and the HIV antigen concentration in the culture liquid was measured.

(i) 4g of the agent was put in the column (volume 10 ml; inner diameter 15 mm) made of polypropylene and then the column was filled with saline solution.

(ii) The filled column was sterilized by autoclaving.

(iii) The saline solution in the sterilized column was replaced by RPMI-1640 medium adequately.

(iv) 50 ml of the HIV culture liquid (RPMI-1640 medium containing 10% FBS) (pH: 7.4) was circulated through the column at the rate of 7 ml/min for 1 hour.

(v) After the circulation, the HIV antigen concentration in the culture liquid was measured.

The results are shown in Table 7.

TABLE 7

| No. | Agent | HIV antigen in the culture liquid (ng/ml) | HIV (p24) antigen removal (%) |
|---|---|---|---|
| — | Positive control | 80.00 | 0 |
| Comp. Ex. 1 | Polypropylene | 76.96 | 3.8 |
| Example 3 | Silica-alumina | 3.38 | 95.8 |
| Example 5 | Cation-exchange resin (COOH-type) | 3.14 | 96.5 |
| Example 6 | Cation-exchange resin (SO₃H-type) | 2.78 | 96.1 |

As can be seen from Table 7, the HIV antigen was eliminated effectively from the HIV culture liquid by the circulation system.

(vi) They were further inoculated on CEM, and the antigen concentrations and antigen productions through indirect immunofluorescence after 7, 14 and 21 days were observed. The results are shown in Table 8. In Table 8, antigen concentrations are expressed as (+), (±) and (−) for values exceeding 0.04 ng/ml, values between 0.03 and 0.04 and values 0.03 ng/ml or below respectively.

As shown in Table 8, antigen productions by specimen solutions treated by the circulation system using minimodule are all (−) as determined by indirect immuno fluorescence technique, showing that HIV can highly and effectively be removed.

TABLE 8

| No. | Agent | Days after incubation | Evaluated by | Dilution ratio $10^0$ | $10^{-1}$ | $10^{-2}$ | $10^{-3}$ | $10^{-4}$ | $10^{-5}$ |
|---|---|---|---|---|---|---|---|---|---|
| Comp. Ex. 1 | Polypropylene | 7 | (a) | + | + | + | + | ± | − |
| | | | (b) | + | + | + | ± | − | − |
| | | 14 | (a) | + | + | + | + | + | − |
| | | | (b) | + | + | + | ± | − | − |
| | | 21 | (a) | + | + | + | + | + | − |
| | | | (b) | + | + | + | ± | − | − |
| Example 3 | Silica-alumina | 7 | (a) | − | − | − | | | |
| | | | (b) | + | − | − | | | |
| | | 14 | (a) | − | − | − | | | |
| | | | (b) | ± | − | − | | | |
| | | 21 | (a) | − | − | − | | | |
| | | | (b) | − | − | − | | | |
| Example 5 | Cation-exchange resin (COOH-type) | 7 | (a) | − | − | − | | | |
| | | | (b) | + | − | − | | | |
| | | 14 | (a) | − | − | − | | | |
| | | | (b) | ± | − | − | | | |
| | | 21 | (a) | − | − | − | | | |
| | | | (b) | − | − | − | | | |
| Example 6 | Cation-exchange resin ($SO_3H$-type) | 7 | (a) | − | − | − | | | |
| | | | (b) | ± | − | − | | | |
| | | 14 | (a) | − | − | − | | | |
| | | | (b) | − | − | − | | | |
| | | 21 | (a) | − | − | − | | | |

TABLE 8-continued

| No. | Agent | Days after incubation | Evaluated by | Dilution ratio | | | | | |
|---|---|---|---|---|---|---|---|---|---|
| | | | | $10^0$ | $10^{-1}$ | $10^{-2}$ | $10^{-3}$ | $10^{-4}$ | $10^{-5}$ |
| | | | (b) | — | — | — | | | |

Note:
Evaluation method
(a): indirect immunofluorescence technique
(b): antigen concentration measurement
Expression of antigen concentration:
(+): 0.04 ng/ml or higher
(±): 0.04 to 0.03 ng/ml
(−): 0.03 ng/ml or below (4) Evaluation of the safety of the agents Silica-alumina (Example 3), cation-exchange resin (COOH-type) (Example 5) and cation-exchange resin (SO$_3$H-type) (Example 6) were treated in RPMI-1640 medium for 20 minutes at 121°C. to give an extract, respectively. Each of the extracts was added to the CEM cells and the cytotoxicity was examined. As a result, in all extracts, 90–95% of the CEM cells were viable after 21 days from the addition of the extract to the cells. This indicates that the above agents are safe to living cells.

COMPARATIVE EXAMPLE 4

Experiments similar to Example 1 were conducted using a cation-exchange resin Dowex 50WX8 (Dow Chemical; surface pH: 2.0) and an anion-exchange resin IRA-75 (Japan Organo Co; surface pH: 12.0). An increase in viscosity of the culture liquid was observed in both cases. This indicates that an undesirable phenomenon (coagulation of plasma) can occur when the plasma of patients is treated with these ion-exchange resins. Hence, the use of substances with a strongly acidic or strongly alkaline surface is not included in this invention.

EXAMPLES 9 through 14

Silica sol (made by Nissan Kagaku Kogyo KK; silica concentration: 21.5 wt%) and alumina sol (made by Nissan Kagaku Kogyo KK; alumina concentration: 16.5 wt%) were mixed in compositions shown in Table 9. Each of the mixtures was heated on a hot plate to remove moisture by evaporation. The residue was calcined in an electric oven at 550°C. for 3 hours. The silica-alumina thus obtained (0.1 g) was immersed in 2 ml of RPMI-1640 liquid medium (concentration: 1.02 g/dl) and the mixture was subjected to autoclave sterilization at 121°C. for 20 minutes. To the thus sterilized mixture was added 1 ml of culture supernatant of HIV-infected CEM cells - RPMI culture medium and the mixture was stirred for 30 minutes and then submitted to testing of the ability for absorbing HIV.

The supernatant of the specimen was taken and filtered through a 0.45 μm filter. HIV (p24 antigen) concentration in the filtrate was measured by ELISA in the same manner as before. The results are shown in Table 9.

TABLE 9

| No. | Si/Al atomic ratio | Antigen conc. (ng/ml) |
|---|---|---|
| Control | — | 1.70 |
| Example 9 | 0.0 | 0.33 |
| Example 10 | 0.19 | 0.59 |
| Example 11 | 0.38 | 0.60 |
| Example 13 | 1.12 | 0.66 |
| Example 13 | 3.70 | 0.24 |

TABLE 9-continued

| No. | Si/Al atomic ratio | Antigen conc. (ng/ml) |
|---|---|---|
| Example 14 | 25.00 | not detected |

From this table it is clear that the ability for removing HIV in the case of silica-alumina is more marked in the region where the Si/Al atomic ratio is higher.

EXAMPLES 15 THROUGH 21

Hydroxyapatite is used as a material for implanting and is superior in biocompatibility.

Having studied removing agents which can maintain the biocompatibility of hydroxyapatite and at the same time exhibit high removing activity of HIV, the present inventors have found that removing agents having high activity are obtained from among hydroxyapatite-silica-alumina 3-component calcined products.

Hydroxyapatite was immersed in a series of silica sol and alumina sol in amounts to attain prescribed concentrations. Each of the mixture was heated to remove moisture by evaporation and the residue was calcined in an electric oven at 550°C. for 3.

0.5 g each of the removing agents thus obtained was immersed in 2 ml of RPMI-1640 liquid medium and the mixture was subjected to autoclave sterilization at 121° C. for 20 minutes. To the thus sterilized mixture was added 1 ml of culture supernatant of HIV-infected CEM cells-RPMI liquid medium and the mixture was stirred for 30 minutes and then submitted to testing on the ability for removing HIV.

The supernatant of the specimen was taken and filtered through a 0.45 μm filter. HIV (p24 antigen) concentration in the filtrate was measured by ELISA in the same manner as before. The result is shown in Table 10.

TABLE 10

| No. | SiO$_2$—Al$_2$O$_3$ % | HIV Antigen Conc. (ng/ml) |
|---|---|---|
| Control | — | 6.0 |
| Example 15 | 0 | 3.6 |
| Example 16 | 5 | 0.62 |
| Example 17 | 10 | 0.69 |
| Example 18 | 20 | 1.24 |
| Example 19 | 30 | 1.80 |
| Example 20 | 50 | 1.56 |
| Example 21* | 100 | 0.56 |

*Silica-alumina made by Davison Chemical; Si/Al atomic ratio: 4.40

The hydroxyapatite used here was one having a Ca/P ratio of 1.5 and calcined at 550° C. for 3 hours. The particle size was 0.42 to 0.55 mm. Si/Al atomic ratio was 25 (weight ratio of SiO$_2$/Al$_2$O$_3$ charged : 97/3). As is seen from Table 10, the removing ability of hydroxyapatite immersed in silica and alumina and calcined is, as compared with that of hydroxyapatite as it is, higher when the concentration is at a relatively low level of 5 to 10%. The surface areas of the 3-component calcined products of hydroxyapatite-silica-alumina were all 100 $m^2/g$. The fact that the low concentration of silica-alumina causes a high activity is preferred since it leads to a reduction in the amount of silica-alumina used.

EXAMPLES 22 AND 23

A solution of 0.79 wt% polyhydroxyethylmethacrylate (PHEMA) - ethanol was added to silica-alumina (made by Davison Chemical; Si/Al atomic ratio: 4.4) in an amount to attain 1 wt% of PHEMA based on the weight of the silica-alumina. The mixture was heated on a hot water bath to remove methanol by evaporation and the residue was cured at 110° C. for 2 hours.

The ability for removing HIV was evaluated in the same manner as in Example of the removing agent comprising hydroxyapatite-silica-alumina described below. The result is shown in Table 11.

TABLE 11

| No. | PHEMA (wt %) | HIV Antigen Conc. (ng/ml) |
|---|---|---|
| Control | — | 34 |
| Example 22 | 0 | 0.56 |
| Example 23 | 1.0 | not detected (≦0.03) |

As shown in the table it is found that coating with PHEMA increases the ability for removing HIV. While it is theoretically possible to further increase coating concentration of PHEMA, in practice however, a concentration of 1.5 to 2.0% causes blocking of particles, which is not preferred. The coating concentration of PHEMA onto silica-alumina therefore is preferably about 1%.

Accordingly, it is found that HIV and/or its related compounds can be removed without impairing the growth of normal lymphocytes by the present invention. It therefore is expected that by removing HIV and/or its related compounds from body fluids of patients in the aggravating period (it is known that HIV in body fluid rapidly increases in the aggravating period) using the removing agent according to the present invention by the extracorporeal blood circulation system, their clinical condition could be prevented from worsening, and their lives could be prolonged. Such method may also serve as an auxiliary means to medicinal therapies. It is also possible to use the removing agents of the present invention for preventing plasma fraction medicines which are manufactured from blood for transfusion from invasion of viruses, purifying blood medicines, or condensing HIV from blood for clinical inspection.

What is claimed is:

1. A method for removing human immunodeficiency virus, its related compounds, or a combination thereof from body fluids of patients comprising the step of contacting said body fluids with a solid carrier of a 3-component calcinated product of hydroxyapatite-silica-alumina wherein said solid carrier has a pH ranging from 2.5 to 6.9.

2. A method for removing immunodeficiency virus, its related compounds, or a combination thereof from body fluids of patients comprising the steps of:

(a) passing blood taken from a patient in need of such treatment through a column packed with a solid carrier of a 3-component calcinated product of hydroxyapatite-silica-alumina, wherein said solid carrier has a pH ranging from 2.5 to 6.9 to remove human immunodeficiency virus, its related compounds, or a combination thereof, thereby cleansing said blood; and (b) administering said cleansed blood to the patient.

3. A method for removing human immunodeficiency virus, its related compounds or a combination thereof from body fluids of patients comprising the steps of:

(a) separating contaminated blood taken from a patient in need of such treatment into hemocytes and plasma;

(b) passing said plasma through column packed with a solid carrier of a 3-component calcinated product of hydroxyapatite-silica-alumina, wherein said solid carrier has a pH ranging from 2.5 to 6.9 to remove human immunodeficiency virus, its related compounds or both, thereby cleansing said plasma;

(c) combining said cleansed plasma with hemocytes to form cleansed whole blood; and (d) returning said cleansed whole blood to said patient.

4. The method according to claim 3, wherein said contaminated blood is separated by centrifugation.

5. The method according to claim 3, wherein said contaminated blood is separated via a separation membrane.

* * * * *